United States Patent
van Hove

[11] Patent Number: 5,978,711
[45] Date of Patent: Nov. 2, 1999

[54] PACEMAKER SYSTEM WITH IMPROVED LEARNING CAPABILITY FOR ADAPTING RATE RESPONSE FUNCTION

[75] Inventor: Jos W. van Hove, Schiedam, Netherlands

[73] Assignee: Vivatron Medical, B.V., Dieren, Netherlands

[21] Appl. No.: 09/027,660

[22] Filed: Feb. 23, 1998

[51] Int. Cl.$^6$ .................................................. A61N 1/365
[52] U.S. Cl. ................................................. 607/17; 607/25
[58] Field of Search ..................... 607/17, 25, 9

[56] References Cited

U.S. PATENT DOCUMENTS

| | | |
|---|---|---|
| 4,228,803 | 10/1980 | Rickards . |
| 4,972,834 | 11/1990 | Begemann . |
| 5,074,302 | 12/1991 | Poore et al. . |
| 5,303,702 | 4/1994 | Bonnet et al. ............................ 607/20 |
| 5,423,870 | 6/1995 | Olive et al. .............................. 607/18 |
| 5,514,162 | 5/1996 | Bornzin et al. .......................... 607/19 |

*Primary Examiner*—Scott M. Getzow
*Attorney, Agent, or Firm*—Woodcock Washburn Kurtz MacKiewicz & Norris, LLP

[57] ABSTRACT

There is provided a rate responsive pacemaker with the capability of dynamically changing the rate response control algorithm. Periodic measurements of the rate response correlation function provide information for determining any desired adjustment to the correlation function. A learning routine tracks changes in the measurements, and from this history automatically adjusts the interval between measurements to optimize the frequency of such measurements. The pacemaker of this invention further provides for an improved adaptation of the rate response function post-implant, by providing for multiple measurements and rate function adjustments daily in order to more quickly adapt the initially set function to patient conditions.

13 Claims, 5 Drawing Sheets

PACEMAKER SYSTEM WITH IMPROVED LEARNING CAPABILITY FOR ADAPTING RATE RESPONSE FUNCTION

FIELD OF THE INVENTION

This invention relates to cardiac pacemaker systems and, more particularly, rate responsive pacemaker systems which have the capability of adjusting the rate response to rate demand as indicated by one or more sensed patient parameters.

BACKGROUND OF THE INVENTION

Rate responsive pacemakers have gained wide acceptance as providing a response which is adaptable to a patient's physiological needs. Normally, as a patient undertakes exercise or becomes involved in a situation which calls for an increased heart rate, the patient's normal feedback mechanisms provide for the increased rate, whereby more blood is delivered by the heart. However, such rate feedback mechanisms may be impaired. Further, even if the heart's natural pacemaker adapts to changing demand, a single chamber pacemaker would be unresponsive to desired rate changes. The rate responsive pacemaker provides a substantially physiologic pacing rate by sensing one or more patient parameters, and correlating desired rate with such one or more parameters to mimic the natural feedback mechanisms. Rate responsive pacemakers can be single chamber, e.g., VVIR; dual chamber, e.g., DDDR; or even multiple chamber.

The first commercially available form of single chamber rate responsive pacemaker was the QT driven rate responsive pacemaker, marketed by the assignee of this invention. See U.S. Pat. No. 4,228,803, Rickards. Subsequently, other pacemakers utilizing other monitored variables have been introduced commercially, e.g., the Activitrax and other activity sensor-based models manufactured by Medtronic, Inc. Whatever the monitored parameter or parameters for indicating desired pacing rate, the general control of the rate responsive pacemaker is common and generic. A rate responsive pacemaker incorporates one or more sensors adapted to sense patients variables which continually indicate, or reflect the patient's cardiac output needs, and from which quantitative information can be derived. For example, in the QT pacemaker, the sensor is the same lead that delivers the pacing pulses. Following delivery of a pacing pulse, it senses the stimulus-evoked T-wave, and provides an electrical signal which can be compared in the time domain to the stimulus pulse, thereby providing the QT time interval information. Dual sensor rate responsive pacemakers use two sensors for monitoring two different parameters, the two parameter signals being combined to advantageously utilize the information from each. Thus, the assignee of this invention makes a dual sensor rate responsive pacemaker which uses both QT interval and activity counts to provide the rate information. Hereafter, the terms "rate responsive parameter", "rate parameter" and "sensor" refer to and incorporate either a single sensor, dual sensor or multiple sensor system.

The general structure of a rate responsive pacemaker also includes a means for carrying out an algorithm by which the pacemaker determines the indicated pacing rate on the basis of information delivered by the sensor. The function of the algorithm is to provide a correlation between the sensed rate parameter and pacing rate, so that the pacemaker is accurately responsive to the monitored information. Using the QT driven rate responsive pacemaker as an example, the algorithm determines, for the current pacing rate, the desired change in pacing rate per ms change in stimulus-T interval, which is defined as slope. In mathematical terms, the algorithm provides the function of rate vs. QT, over a range which is bounded at a lower rate limit (LRL) and an upper rate limit (URL). For an activity-based pacemaker, the algorithm provides the function of rate vs. activity count, for the range between LRL and URL. The algorithm is suitably stored as data in memory, from which the pacemaker can find on a cycle-to-cycle basis what the change in pacing rate should be for a sensed rate parameter change. While the algorithm is initially stored in the pacemaker at implant, or programmed at time of implant, it is known that the correlation between pacing rate and the rate parameter can change for any patient. For this reason, the pacemaker should have the capacity to test and adapt the rate response function, i.e., the algorithm, as a function of patient history. See U.S. Pat. No. 4,972,834, incorporated herein by reference, which provides for dynamic rate responsiveness by automatic adaptation of the algorithm. As set forth in the referenced patent, the slope of QT vs. pacing rate at LRL is measured each night, and the algorithm is adjusted based on this measurement. Likewise, an activity-based rate responsive pacemaker can undergo a similar daily test for the purpose of adapting the algorithm.

A problem with the daily test of the rate responsive algorithm, as provided in the referenced U.S. Pat. No. 4,972,834, is that the test can be upsetting, since it involves pacing at different rates in order to determine the patient's correlation of pacing rate and sensed parameter at one or more rates; such test pacing can be felt by the patient and be unsettling, especially if undertaken at night. Further, for many patients the pacemaker may normally be on standby at night and not be delivering pace pulses, such that the test involves overdrive pacing which takes additional power. Accordingly, it is desirable to provide the pacemaker with the capability of reducing the frequency of testing the algorithm, e.g., provide for longer intervals between tests when the history of the patient indicates that relatively little adjustment is required on an on-going basis.

SUMMARY OF THE INVENTION

It is a primary object of the invention to provide a rate responsive pacemaker having a dynamic rate response algorithm which is periodically adjusted in accord with tested variations of pacing rate vs. the rate response parameter, and having an improved learning capability for determining a more optimum frequency for testing the algorithm. In accordance with the above object, there is provided a rate responsive pacemaker with a dynamically adjustable algorithm for correlating pacing rate with the sensed parameter, wherein the pacemaker continually determines the measurement period for taking one or more measurements designed to provide information for adapting the rate algorithm. In a preferred embodiment of a QT pacemaker, the test measurement involves detecting a measure of the correlation slope at LRL, whereby the algorithm can be adjusted based on the slope reading. More than one such measurement can be taken during each test, e.g., slope can also be measured around other rates. The pacemaker stores the measured data, and compares it with prior measurement data to determine whether there has been a significant change, or deviation from the prior measurement or measurements. For example, the newly measured slope at LRL is compared with the last such measured slope. If the deviation is greater than a predetermined amount, the measurement period is shortened; if the deviation is less than a predetermined amount, the measurement period may be lengthened. By this technique, the measurement period is adjusted in terms of patient history, and lengthened to an optimally long interval consistent with reliable adaptation of the algorithm to follow patient changes.

The invention also includes an improved fast learning process for adjusting the correlation algorithm following implant. By adjusting the frequency of measurements to include plural measurements nightly, the pacemaker enables a more physiologic onset of rate response and a faster adaptation of the algorithm from the initial algorithm setting to respond to the patient's metabolic needs.

DESCRIPTION OF THE PREFERRED EMBODIMENTS

Figure 1:
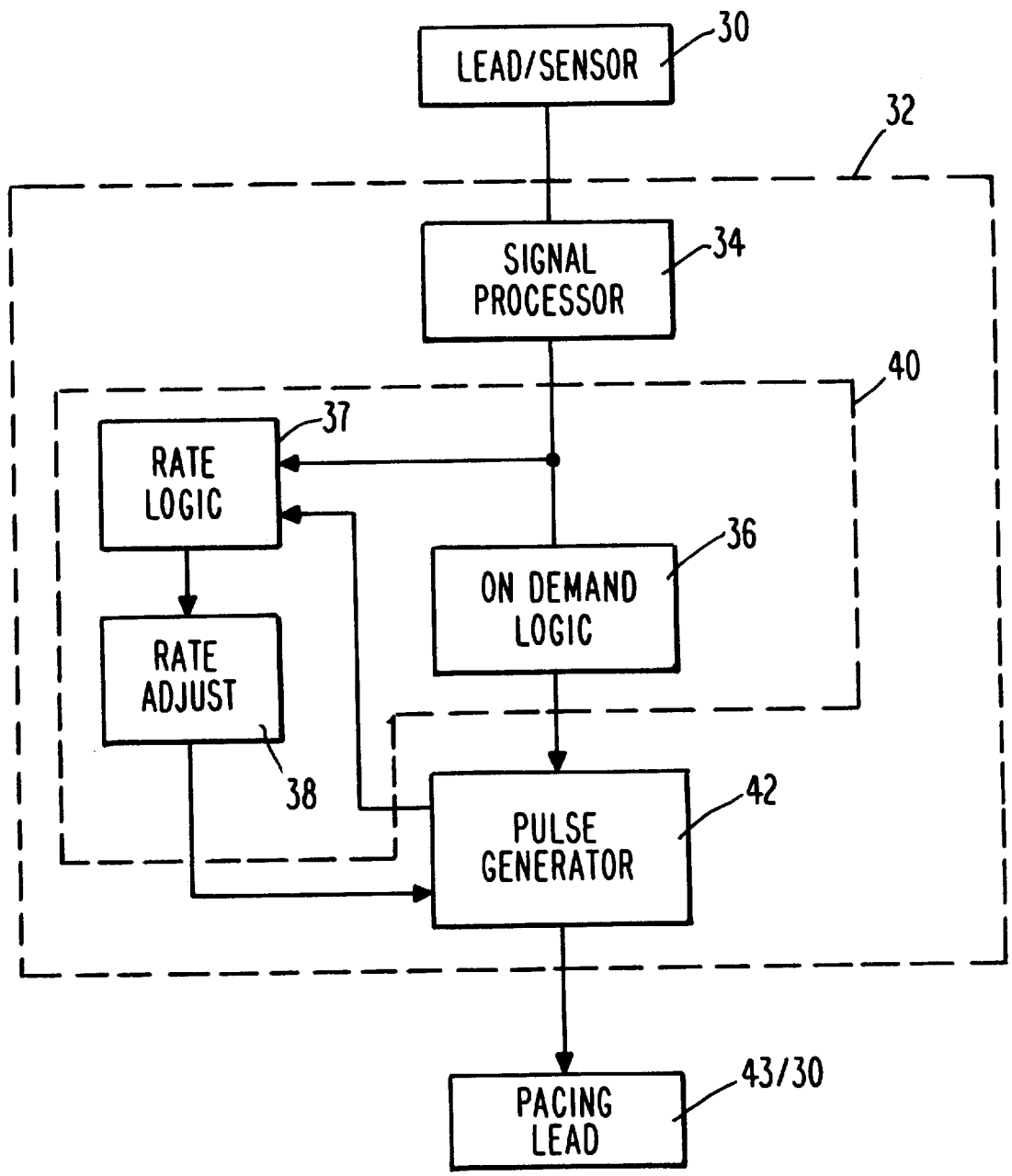
FIG. 1 is a block diagram of a representative rate adaptive pacemaker as can be used in the practice of this invention.

Referring now to FIG. 1, there is shown a block diagram indicating the primary functional components of a rate adaptive pacemaker. A lead or sensor 30 is represented for deriving patient information. As used in this invention, one or more sensors may be utilized to detect one or more patient variables indicative of patient demand for heart rate; reference to the sensor includes dual or multiple sensor configurations. In the preferred QT driven embodiment, the sensor 30 is integral with the lead which is positioned in the ventricle, and senses the T wave response, whereby the QT interval may be obtained in a known manner. Other sensors for sensing other patient variables, including mechanical movement, respiration rate, blood pH, temperature, etc. are known in the pacing art for use in rate responsive pacers, and may be utilized as an embodiment of this invention. The input from the sensor 30 is communicated to the implantable pacemaker 32. The sensor information is passed through conventional signal processor 34 to place it into suitable form for further use in the logic circuitry. Sensed spontaneous heartbeat signals, e.g., QRS senses, are transmitted to on demand logic circuitry 36, for inhibiting the generation of stimulus pulses whenever natural heartbeats occur, in a manner well known in the art. The output of on demand logic block 36 is transmitted to pulse generator 42, which provides the pacemaker output pulses. The output pulses are delivered to a pacing lead 43, which for the QT case is lead 30. It is to be noted that while the invention is illustrated by a single chamber pacemaker, it is applicable to single or dual chamber pacemakers, e.g., VVIR or DDDR pacemakers; and to multiple chamber pacemakers.

In the QT preferred embodiment, the output of signal processing circuit 34, which includes indications of the T wave, is inputted to rate logic block 37 for determining the timing of the T wave relative to a delivered pulse signal, the timing of the latter being provided from pulse generator block 42. The rate logic block also provides for determining the desired pacing rate as a function of QT, or other sensed variable, in a manner described in more detail hereinbelow. The output of rate logic block 37 is transmitted to rate adjust circuit 38, which generates an appropriate control signal which is transmitted to pulse generator 42, to control generator 42 to deliver pacing pulses at a rate, or pacing interval, corresponding to the output of rate logic circuit 37. In the case of the QT driven pacemaker, rate logic block 37 preferably includes stored data correlating values of QT interval with respective values of pacing interval, the ratio of which is defined as "slope." Thus, for a given sensed QT interval, rate logic block 37 provides an output that corresponds to a determined pacing interval at which the pacemaker paces the patient in response to the detected QT interval. For other embodiments which incorporate sensors for one or more other rate parameters equivalent means are incorporated for generating the rate logic and rate adjust circuits. The functions of blocks 36, 37, and 38, indicated together as 40, may be carried out in a CPU or microprocessor, as disclosed in one or more of the referenced patents. The microprocessor and/or associated memory store the rate response function data, which data is used in determining rate in a manner discussed hereinbelow.

Figure 2A:
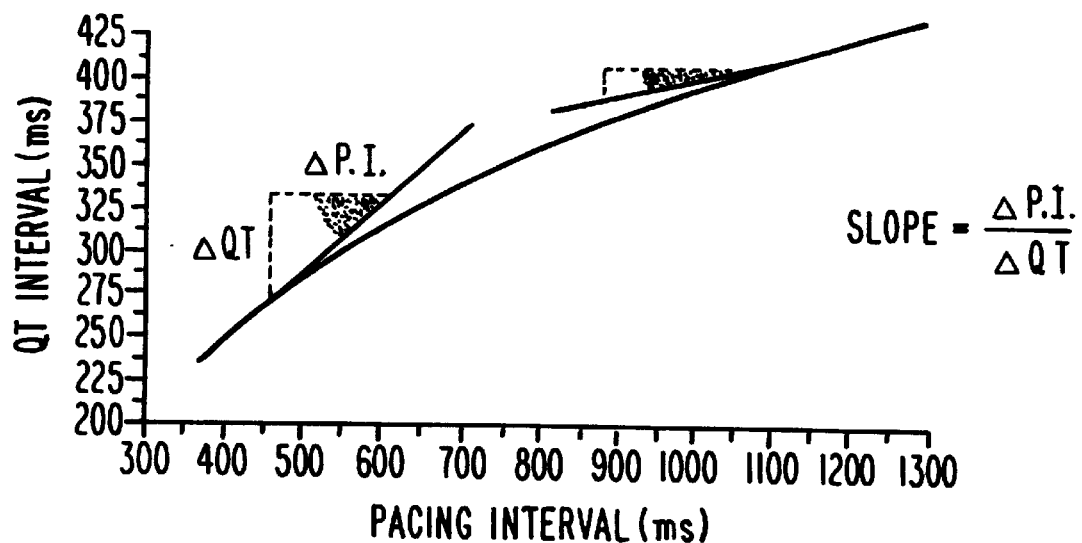
FIG. 2a is a graph of QT vs. pacing interval (PI) for a rate adaptive pacemaker embodiment of this invention where QT is the rate parameter.

Referring now to FIG. 2a, there is shown a graph depicting generally how QT interval (ms) varies as a function of pacing interval (ms) due to physiological variables. As seen, there is depicted a rate-dependent non-linear relationship between QT interval and pacer interval. It has been determined empirically that QT interval as an indicator is influenced by both heart rate alone (which can be seen when the patient is at rest) and also by patient demand, e.g., when a patient undergoes exercise. Stating it alternatively, the relationship between pacing interval and QT interval is a function of two factors, i.e., patient metabolic demand such as induced by exercising, and also the heart rate itself. The resultant graph is seen to be nonlinear, representing a non-linear slope which is defined as incremental change in pacing interval per incremental change in QT. It is seen (FIGS. 2a and 2b) that at high pacing intervals, corresponding to a lower rate, the slope is greater, whereas at lower pacing intervals (corresponding to higher rates) the slope is less. This results from the fact that when a higher rate is implemented by the pacemaker, the shorter P.I. tends to induce a further decrease in QT beyond what was initially indicated by the body's demands. In practice, the degree of QT interval shortening is least at long pacing intervals. If this is not compensated for, there may result a delay before a significant increase in pacing rate is seen after the commencement of exercise in some patients. Further, by lowering the slope as rate is increased, the pacemaker is not driven directly to URL too quickly.

Figure 2B:
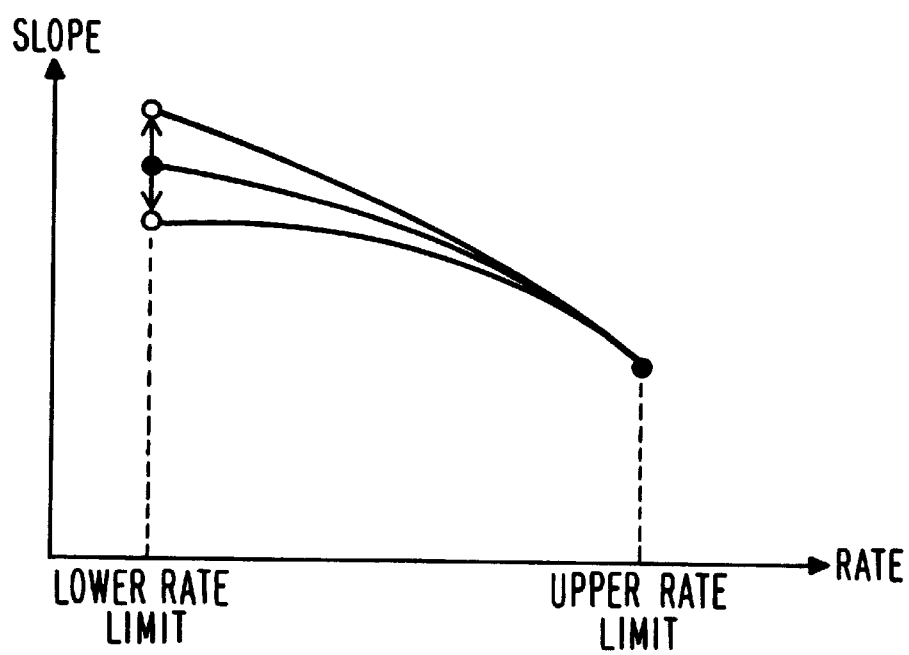
FIG. 2b is a graph indicating slope vs. rate for a QT rate responsive pacemaker, where slope equals $\Delta PI/\Delta QT$.

Referring now to FIG. 2b, the implemented variation in slope at the lower rate limit (LRL) is illustrated in a general manner for a QT rate responsive pacemaker system. In a prior embodiment, the slope at the programmed LRL is automatically measured once a day, when the patient is at rest. This is accomplished by having the pacemaker determine the relationship between the QT interval and the pacing interval at rest, when the following two conditions are fulfilled: (a) the pacemaker is pacing at LRL, and the patient is therefore resting or sleeping; and (b) the pacemaker's internal 24-hour clock indicates that it is nighttime. The relationship, or slope, is determined by incrementally changing the pacing rate about LRL, and detecting the change in QT, so as to get a measurement of slope at about LRL. This value determines the actual desired slope at LRL, and if such slope is different from the previous maximum slope, the slope at the LRL is automatically reprogrammed. Preferably, in order to avoid the possibility of a sudden, harsh change in the programmed slope at LRL, the algorithm only allows the slope to be adjusted in small steps, as indicated in FIG. 2b. Having determined the slope at LRL, the remainder of the curve is automatically adapted to provide a continuous change in slope from LRL to URL, as illustrated.

In general, the slope can be calculated as a function of interval (pacing interval, or escape interval) in a variety of ways. For example, the change in pacing interval for a certain change in sensor input, i.e., slope, may be a simple function of pacing interval. Thus, $$\Delta Esc.\ Int./\Delta QT = f\ (Esc.\ Int.)$$

Figure 3:
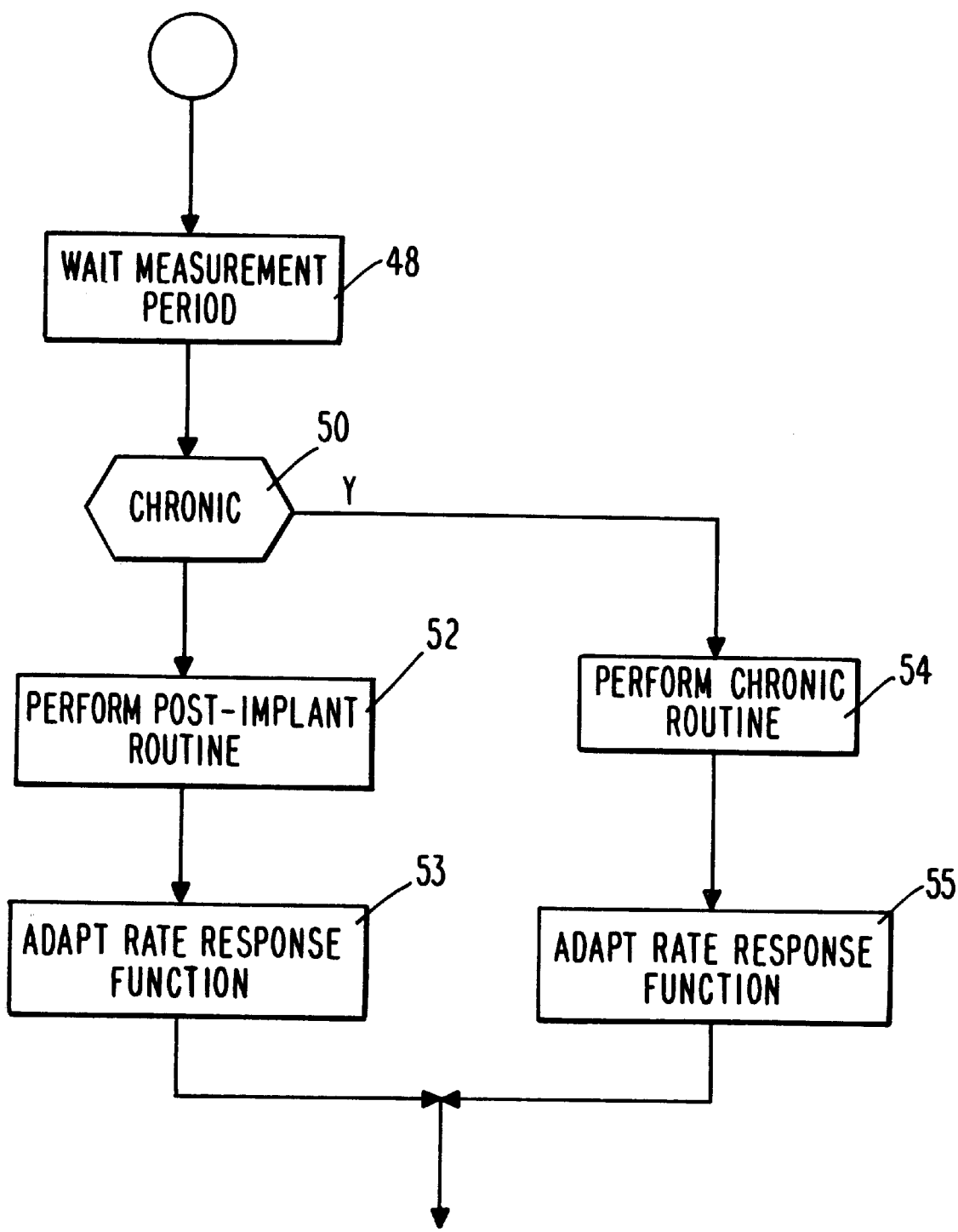
FIG. 3 is a flow diagram showing steps for determining whether the pacemaker should perform a post-implant routine, or a chronic routine for adopting pacing rate and determining the appropriate measurement period for measuring slope at lower rate limit.

Alternately, slope may be a function of change in the sensor input value (i.e., $\Delta QT$), or a function of both the pacing interval and change in sensor input. The algorithm for determining slope is not limited. In the preferred QT embodiment, the function is linear:

Slope=$\Delta QT/\Delta Int.$=A+B (60,000/LRL-Esc. Int.) where $\Delta Int.$=LRL Interval–Esc. Interval, B=curve factor (primary determinant of slope at URL) and A=slope at LRL Referring now to FIG. 3, there is shown a routine carried out for determining whether the implanted pacemaker is in a post-implant mode or a chronic mode. If the pacemaker has just recently been implanted, such that the rate response curve is being adapted from the factory setting, then the pacemaker performs a nightly post-implant routine in order to optimize slope at LRL, and to adjust the overall rate response curve accordingly. On the other hand, if the pacemaker has been implanted long enough that a chronic condition has been reached, a different routine is performed to set the measurement. As seen at step 48, the pacemaker waits for timing out of the current measurement period, e.g., until one or more days have passed and nighttime has been detected. Following this, at 50, it is determined whether the pacemaker has passed through the chronic state. This may be determined either by counting a predetermined number of days after implant, or by analyzing variations in the rate response curve as have been automatically set by the post-implant routine of FIG. 4. If the pacemaker is not yet in the chronic state, the post implant routine is performed as indicated at 52, following which the response function is adapted accordingly, as shown at 53. If the pacemaker is determined to be in the chronic mode, then the chronic routine of FIG. 5 is performed, as indicated at 54, and the rate response function is adapted accordingly, as indicated at 55.

Figure 4:
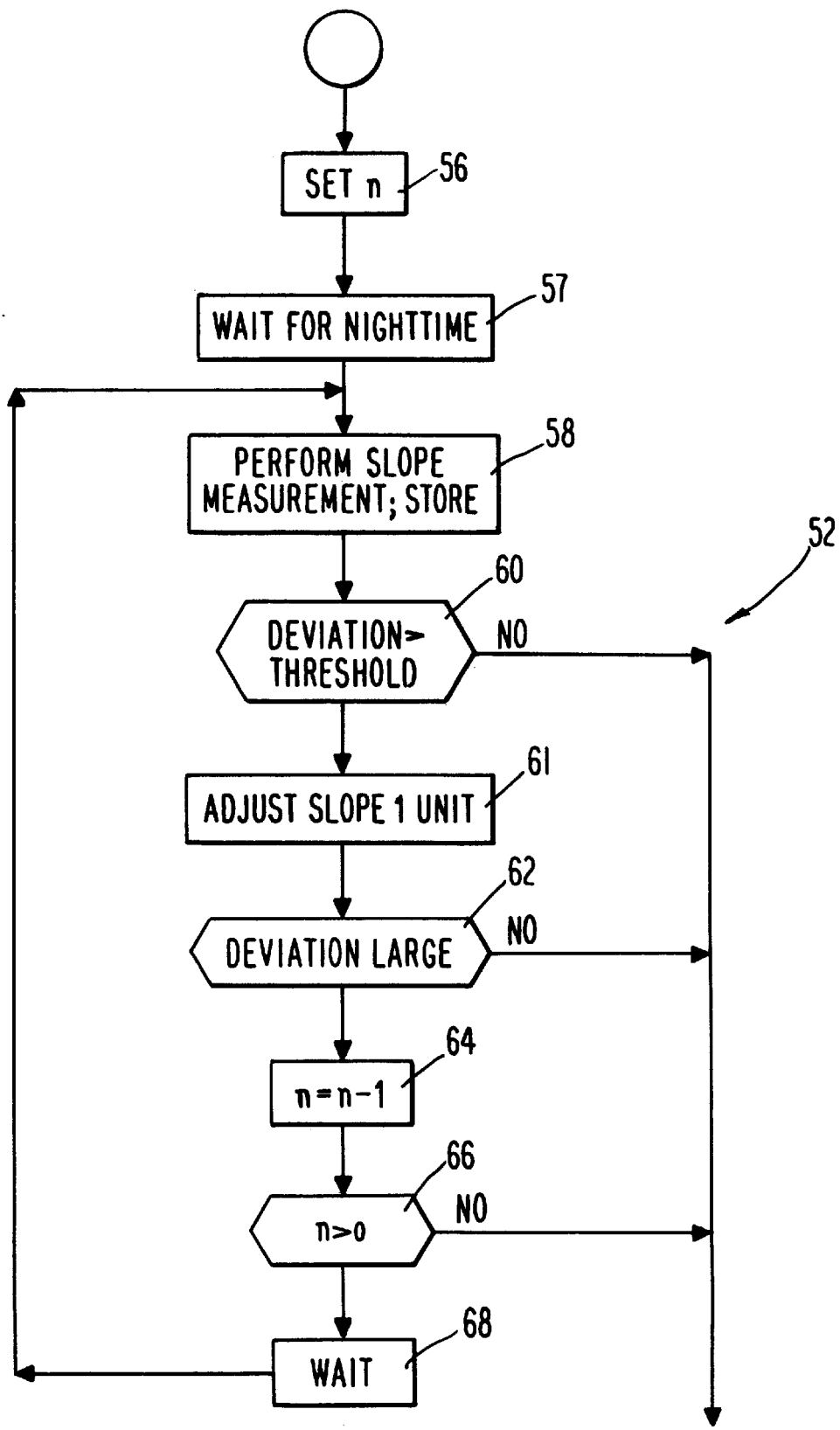
FIG. 4 is a flow diagram representative of the post-implant routine for determining the rate response slope measurement period in accordance with this invention.

Referring now to FIG. 4, there is shown a flow diagram setting forth the primary steps of the post-implant routine 52. At 56, a variable n is set to a predetermined number, e.g. 2 or 3, representative of the maximum number of times that slope can be adjusted during one nighttime. Then, at 57, the pacemaker waits for detection of nighttime, in the manner as discussed in referenced U.S. Pat. No. 4,972,834. At 58, nighttime having been detected, the pacemaker performs a slope measurement, and stores the newly found slope value, $\Delta PI/\Delta QT$. Then at 60 the new value of slope is compared with the prior stored value of slope, and it is determined whether the difference, or deviation, is greater than a predetermined threshold. If no, this means that there is too little deviation to warrant any further change in slope at this time, and the routine exits. However, if the deviation is greater than the stored threshold, the routine goes to 61 and adjusts the slope by one unit, e.g., a programmable value of $\Delta PI/\Delta QT$. Then at 62 it is again determined whether the deviation is large, e.g., whether it is greater than 2× threshold. If not, the routine exits. However, if the deviation is determined to be large, the routine goes to block 64 and decrements n by 1. At 66, n is compared to 0, and if it is 0 the routine exits, since the allowed number of slope adjustments have already been made. However, if n remains greater than 0, the routine goes to 68 where the pacemaker waits a predetermined time interval, e.g., one hour, and then performs another slope measurement and stores the value. The routine loops back to 58 and continues until it exits. By this means, during the post-implant period, the slope can be adjusted more than one time a night, to speed up adaptation of the rate response curve from its initial factory setting.

Figure 5:
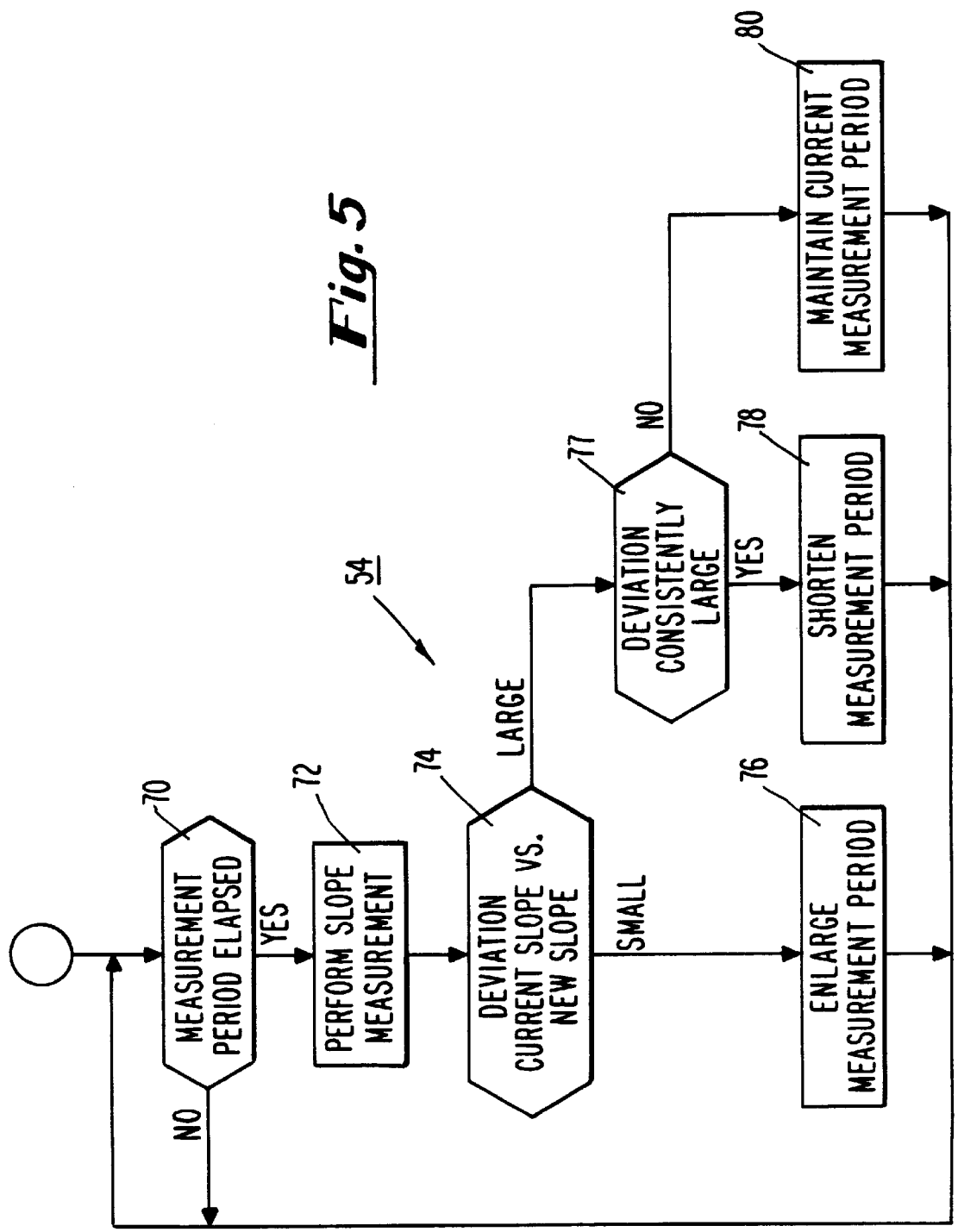
FIG. 5 is a flow diagram of the chronic routine for determining the rate response slope measurement period in accordance with this invention.

Referring now to FIG. 5, there is shown a flow diagram illustrating the primary steps taken in the chronic routine 54 for adapting the measurement period for changing the slope to lower rate limit. The routine is entered whenever the pacemaker is in the chronic state as determined at step 50 in FIG. 3. At 70, it is determined whether the measurement period has elapsed, e.g., if the measurement is two days, then the period has elapsed when two days have passed since the last measurement and it is again nighttime. When this condition is found, the routine goes to block 72 and performs the slope measurement, and stores this value. At 74, the newly determined slope value is compared with the current, or prior value, to obtain the deviation. The deviation is compared to a predetermined number, and found to be either small or large. If small, the routine goes to 76 and enlarges the measurement period, e.g., it can go from two to three days. However, if the deviation is large, the routine goes to block 77, and determines if deviation has been conssitently large. If yes, at 78 the routine shortens the measurement period, e.g., it may go from two days back to one day, or from x days to x–1 days. If no, the routine maintains the current measurement period, as shown at 80. Although not shown, step 74 may include a determination that the deviation is within limits, i.e., less than plus or minus a threshold value, in which case the measurement period is determined to be optimal, and the routine exits without any change.

It is to be understood that other routines for adapting the measurement period as a function of patient history are within the scope of the invention. Thus, by way of example, instead of comparing the new slope with the prior slope, a running average of slope can be stored, and the new slope compared with such running average. Further, more complex schemes are within the invention, e.g., when a deviation of slope at one rate is greater than a predetermined value, one or more additional measurements may be taken at different rates. In all such examples, the important feature is to adjust the frequency of measurements based on patient history, so as to optimize the rate of dynamically adjusting the rate response algorithm.

I claim:

1. A rate responsive pacemaker system for delivering pacing pulses to a patient's heart at a rate which is adjusted in response to the patient's condition, comprising:

pulse generator means for generating pacing pulses;

rate control means for controlling said pulse generator means to generate pacing pulses at a rate responsive to the patient's condition, having parameter means for sensing a least one patient parameter and function means for determining pacing rate as an adjustable response function of said at least one patient parameter;

measurement means for measuring a variation of said at least one parameter with pacing rate, and enabling means for periodically enabling said measurement means;

adjusting means for adjusting said response function to adapt it to a said measured variation; and timing means for timing the periodicity of enabling said measurement means.

2. The system as described in claim 1, wherein said timing means comprises means for storing a record of said variations following each measurement thereof, means for comparing each said measured variation with the last prior such measured variation, and means for setting said periodicity as a function of said comparing.

3. The system as described in claim 2, wherein said comparing means comprises means for determining whether the difference between successive measured variations is greater or less than a predetermined value, and said timing means has enlarging means for enlarging the timing period of said measurements when said difference is less than said predetermined value.

4. The system as described in claim 1, comprising means for measuring QT interval, and wherein said parameter is QT interval and said measuring means comprises means for measuring incremental variation of QT per incremental change of pacing rate at at least one predetermined pacing rate.

5. The system as described in claim 4, comprising means for limiting pacing rate to a lower rate limit, and wherein said measuring means comprises means for measuring said incremental variation at said lower rate limit.

6. The system as described in claim 5, comprising means operative after implant of said system for enabling multiple said measurements per day as a function of said comparing.

7. The system as described in claim 5, wherein said timing means has means for reducing the period between measurements when said comparing indicates a difference in variations greater than a predetermined value.

8. The system as described in claim 5, wherein said timing means has means for increasing the period between measurements when said comparing indicates a difference in variations less than a predetermined value.

9. A rate responsive pacemaker system, comprising:

pulse means for generating and delivering pace pulses at an adjustable rate to a patient's heart;

rate response means for adjusting said rate as a predetermined function of at least one patient parameter, having parameter means for determining said at least one parameter, a stored function relating said parameter to pacing rate, and means for changing said function;

test means for periodically testing to determine if said function is to be changed, and storage means for storing representations of said tests; and interval means for automatically setting the time interval of said periodic testing as a function of said stored representations.

10. The system as described in claim 9, wherein said test means comprises means for obtaining a measure of said parameter in response to pacing at about at least one predetermined pacing rate and storing said measure, and wherein said interval means comprises comparing means for comparing successive said stored measures from successive stored tests.

11. The system as described in claim 10, where said test means comprises means for obtaining a measure of the ratio of change of said parameter per incremental change of pacing rate around said predetermined rate.

12. The system as described in claim 10, wherein said parameter means comprises means for obtaining a value of QT interval after each delivered pace pulse, and said test means comprises means for obtaining a measure of the ratio of change of QT per incremental change of pacing rate at said predetermined rate.

13. A method of periodically adjusting the rate response function in a rate responsive pacemaker, said pacemaker having the feature of determining pacing rate as an adjustable function of at least one sensed patient parameter, comprising:

measuring a variation of said at least one parameter with pacing rate;

adjusting said rate response function to adapt it to a said measured variation;

storing each said measured variation, and comparing each said measured variation with at least the last such prior measured variation; and timing the occurrence of the next said measuring step as a function of said comparing.

\* \* \* \* \*